United States Patent [19]

Marumoto et al.

[11] 4,341,769

[45] Jul. 27, 1982

[54] 2,6-DIAMINONEBULARINES, THEIR PRODUCTION AND USE

[75] Inventors: Ryuji Marumoto, Ashiya; Shunsuke Shima, Minoo; Masao Tanabe, Osaka, all of Japan

[73] Assignee: Takeda Chemical Industries, Ltd., Osaka, Japan

[21] Appl. No.: 250,297

[22] Filed: Apr. 2, 1981

[30] Foreign Application Priority Data

Apr. 14, 1980 [JP]   Japan ................................. 55-49432

[51] Int. Cl.³ ....................... A61K 31/70; C07H 19/16
[52] U.S. Cl. ...................................... 424/180; 536/24; 536/26
[58] Field of Search ...................... 424/180; 536/24, 26

[56] References Cited

U.S. PATENT DOCUMENTS 4,109,078  8/1978  Vorbrüggen ........................... 536/24
4,258,033  3/1981  Marumoto et al. .................... 536/26

*Primary Examiner*—Blondel Hazel
*Attorney, Agent, or Firm*—Wenderoth, Lind & Ponack

[57] ABSTRACT

Novel $N^2$-substituted-2,6-diaminonebularines of the formula:

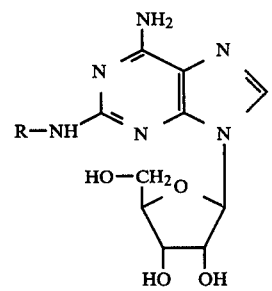

wherein R is 2-pyridyl or 3-pyridyl, which may be substituted, or acid addition salts thereof have an excellent coronary vasodilator action.

10 Claims, No Drawings

2,6-DIAMINONEBULARINES, THEIR PRODUCTION AND USE

The present invention relates to novel $N^2$-substituted 2,6-diaminonebularines having excellent pharmacological action. More particularly, this invention relates to $N^2$-pyridyl-2,6-diaminonebularines of the formula;

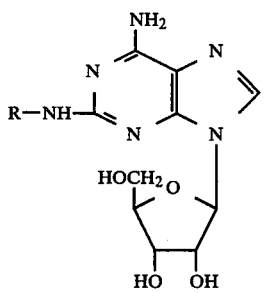

wherein R is 2-pyridyl or 3-pyridyl, which may be substituted, or acid addition salts thereof, which have an excellent coronary vasodilator action.

Thus, the principal object of the present invention is to provide the novel 2,6-diaminonebularine derivatives (I) and acid addition salts thereof which show an excellent coronary vasodilator action, and another object is to provide pharmaceutical compositions comprising one or more of these compounds. A further object is to provide an industrially feasible method for producing these compounds. Other objects will be made clear from the description and claims presented hereinafter.

Referring to the above general formula (I), 2-pyridyl or 3-pyridyl as represented by R may have one or more substituents such as lower alkyl (e.g. methyl, ethyl, propyl, i-propyl, butyl, i-butyl, t-butyl, etc.; preferably $C_{1-4}$), lower alkoxyl (e.g. methoxy, ethoxy, propoxy, butoxy, etc.; preferably $C_{1-4}$), substituted and unsubstituted amino (e.g. amino methylamino, dimethylamino, ethylamino, anilino; preferably unsubstituted amino, amino substituted with one or two $C_{1-2}$ alkyl or phenyl), etc.

Of the above-mentioned compound (I), preferred species are those having for R an unsubstituted 3-pyridyl group or a 3-pyridyl group carrying one or more of said substituent groups on the 5- or/and 6-position.

The compound (I) can be easily produced by the following process, for instance.

A compound of the formula;

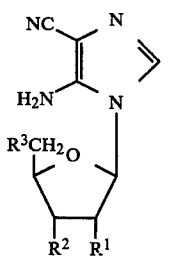

wherein $R^1$, $R^2$ and $R^3$, independently of one another, are hydroxyl or protected hydroxyl is reacted with a compound of the formula;

R—NHCN (III)

wherein R is as defined hereinbefore, or a compound of the formula;

R—NHC(X)=NH (IV)

wherein R is as defined above and X is amino which may be substituted or lower alkylthio, and removing the hydroxyl-protecting groups of the resulting compound when such protective groups remain, to give compound (I).

Protective groups on protected hydroxyl groups $R^1$, $R^2$ and $R^3$ in formula (II) may for example be carboxylic acid-derived acyl groups (which may be aliphatic, aromatic or heterocyclic acyl groups and may be either saturated or unsaturated; e.g. acetyl, propionyl, caproyl, palmitoyl, benzoyl, toluoyl, furoyl, etc.), nitro, sulfonyl, isopropylidene, alkoxyalkylidene, etc. Especially preferred are acyl groups derived from aliphatic or aromatic carboxylic acids of up to 7 carbon atoms, particularly preferred is propionyl. $R^1$, $R^2$ and $R^3$ may all be protected or only some of them, e.g. $R^1$ and $R^2$, may be protected. Or all of $R^1$, $R^2$ and $R^3$ may be unprotected hydroxyl groups. Most of such protective groups are usually removed on reaction of compound (II) with either compound (III) or compound (IV), but when such protective groups remain, they can be easily removed by per se conventional procedures, for example by treatment with a base (aqueous ammonia, alkali metal) in the case of carboxylic acid-derived acyl groups, catalytic reduction in the case of nitro, or treatment with an acid (e.g. formic acid, acetic acid, hydrochloric acid) in the case of isopropylidene, for instance.

The above cyanamide compound of formula (III) can be easily prepared by the procedure described in Berichte der Deutschen Chemischen Gesellschaft, 18, 3217–3234 (1885) or a procedure analogous thereto, for instance.

Referring to general formula (IV), X is amino or subtituted amino, or lower alkylthio. The substituent on the amino group is preferably the same group as R but may be a different one. The lower alkyl moiety or said lower alkylthio is preferably a group of up to 4 carbon atoms, such as methyl, ethyl, isopropyl, butyl, t-butyl, etc. Among the compounds represented by the formula (IV), guanidine compounds can be easily prepared by for example the procedures described in Journal of the American Chemical Society, 51, 477 (1929) and Khimiya Geterotsiklicheskikh Soedinenii, 7, 249 (1971) or any procedure analogous thereto. S-Alkylisothiourea compounds can be easily prepared by the procedure described in Berichte der Deutschen Chemischen Gesellschaft, 14, 1489 (1881) or any procedure analogous thereto.

It is generally preferable to react at least an equimolar and preferably about 2 to 5 equivalents of (III) with each equivalent of (II). Generally this reaction is preferably conducted in the presence of a base. The base may for example be ammonia, a primary to tertiary amine which is preferably a compound having low-boiling point (inclusive of cyclic amines; e.g. n-propylamine, i-propylamine, n-butylamine, i-butylamino, t-butylamine, triethylamine, pyridine, picoline, 2,6-lutidine), sodium or potassium methoxide (e.g. sodium methoxide, sodium ethoxide, sodium methoxyethoxide, potassium t-butoxide) and so forth, although ammonia is preferred. Such a base is usually employed in a proportion of about 10 to 100 equivalents with respect to compound (II).

Generally this reaction is preferably conducted in a solvent. The solvent may be any organic solvent that will not interfere with the contemplated reaction, such as lower alkanol (methanol, ethanol, propanol), tetrahydrofuran, dioxane, dimethylformamide or a mixture thereof. Generally this reaction can be conducted with advantage at an elevated temperature of about 100° to 200° C. and preferably in a sealed reaction vessel.

In the process, of reacting a compound (II) with a compound (IV), (IV) is preferably employed in a proportion of at least an equimolar, preferably about 2 to 5 equivalents, with respect to (II). Generally, this reaction proceeds with advantage in the presence of an amine of the following formula (V) or a derivative thereof:

RNH$_2$ (V)

wherein R is as defined hereinabove.

However, this is not an essential requirement. Moreover, the reaction may be carried out in the presence of a solvent. The solvent may be any organic solvent that will not interfere with the reaction, such as alkanols (e.g. butanol, hexanol, octanol), dioxane, dimethylformamide, dimethylacetamide, dimethylsulfoxide, ethylene glycol (e.g. ethylene glycol, ethylene glycol diethyl ether, ethylene glycol monoethyl ether, ethylene glycol monomethyl ether, diethylene glycol monomethyl ether, diethylene glycol, diethylene glycol dimethyl ether) secondary or tertiary amine (inclusive of cyclic amines, e.g. diethanolamine, triethylamine, pyridine, N-methylpyrrolidone, morpholine, piperidine) or a mixture thereof. When such a solvent is employed, it is used in a proportion of 1 to 50 times, preferably 5 to 15 times, the amount of (II) (w/v). Generally, this reaction proceeds well at an elevated temperature of about (50° to 250° C. and preferably about 100° to 200° C. While the reaction may be conducted at an elevated pressure, it is more advantageous to conduct the reaction at atmospheric pressure. When protective groups remain on the hydroxyl groups of product compound, the protective groups can be easily removed by the above-mentioned procedure to obtain (I).

The starting compound (II) can be prepared in two or three steps and in good yield from 5-amino-1-β-D-ribofuranosylimidazole-4-carboxamide, which is readily available as a fermentation product, for example by the procedure described in U.S. Pat. No. 3,450,693 or a procedure analogous thereto.

The resultant N$^2$-pyridyl-2,6-diaminonebularine (I) can be easily isolated from the reaction mixture by a procedure known per se. For example, the excess reactants and solvent are distilled off and the residue is washed with lower alkanol or the like and is recrystallized from water, lower alkanol or mixture thereof to give (I) as a pure product. This compound (I) can also be obtained as a salt, for example a physiologically acceptable acid addition salt, e.g. mineral acid salt (e.g. hydrochloride, sulfate), by a procedure which is known per se.

The N$^2$-pyridyl-2,6-diaminonebularines (I) and salts thereof according to this invention are novel compounds and have excellent coronary vasodilator action, besides without side-effects such as hypotensive effect and being low in toxicity, and are of value, for example, as drugs for the treatment of ischemic heart diseases such as coronary insufficiency, angina pectoris, myocardial infarction and the like in mammals (pet animals such as dog and cat; laboratory animals such as rat and mouse; and man, etc.)

When the compound of this invention is used for such medicinal purposes, it can be orally or parenterally administered either as it is or in admixture with suitable pharmaceutically acceptable carriers, vehicles or diluents, in such dosage forms as powders, granules, tablets, capsules, injections, etc. The dosage depends on the disease to be managed and the route of administration. However, the advantageous dosage for the treatment of coronary insufficiency in an adult human, for instance, is about 1 to 10 mg. daily by the oral route or about 0.05 to about 0.5 mg. daily by the intravenous route.

The following reference, working and experimental examples are further illustrative but by no means limitative of this invention.

REFERENCE EXAMPLE 1

A solution of 12 g of 3-amino-6-ethoxypyridine in 30 ml of acetone was admixed with a solution of 7.6 g of potassium thiocyanate in 60 ml of acetone, and under stirring, 15.4 g of benzoyl chloride was added dropwise. The mixture was then boiled for 10 minutes. The reaction mixture was poured into ice-water and the resulting crystals (m.p. 130°–133° C.) were recovered by filtration and boiled with 50 ml of 10% sodium hydroxide for 15 minutes. After cooling, crystals (m.p. 142°–146° C.) of 6-ethoxy-3-pyridylthiourea were obtained. These crystals were dissolved in 150 ml of hot 10% potassium hydroxide, and after addition of 37 g of lead acetate, the mixture was stirred at 80° C. for 20 minutes. The precipitated lead sulfide was filtered off and the filtrate was neutralized to give 5 g of 6-ethoxy-3-pyridylcyanamide as colorless needles melting 102°–104° C.

In the same manner as above, there were obtained the 2-pyridylcyanamides and 3-pyridylcyanamides listed in Table 1.

TABLE 1

| R | M.P. (°C.) |
|---|---|
| ![CH3-pyridyl] | 156–157 |
| ![CH3O-pyridyl] | 113–115 |
| ![pyridyl] | 138–142 |
| ![PhNH-pyridyl] | 70–75 |
| ![CH3-pyridyl isomer] | 183–184 |

TABLE 1-continued

| R—NHCN | |
|---|---|
| R | M.P. (°C.) |
| CH₃-pyridyl (4-methyl-2-pyridyl) | 247–250 |
| CH₃-pyridyl (5-methyl-2-pyridyl) | 220–224 |
| pyridyl-CH₃ (6-methyl-2-pyridyl) | 225–226 |
| CH₃,CH₃-pyridyl (4,6-dimethyl-2-pyridyl) | 223–224 |
| pyridyl | 152–153 |

REFERENCE EXAMPLE 2

A mixture of 5 g of 3-aminopyridine and 12.5 g of S-methylisothiourea sulfate was fused at 180°–190° C. for 3.5 hours. To the resultant tarry product was added 50 ml of water. The insoluble materials were filtered off and 50 g of ammonium nitrate was added to the filtrate to deposit 4.15 g of 3-pyridyl guanidinium nitrate as brown needles, m.p. 209°–214° C. (decomp.).
Mass spectrum: 126 (molecular ion peak)

EXAMPLE 1

To 4.8 g of 5-amino-1-β-D-ribofuranosyl-4-cyanoimidazole and 4 g of 3-pyridylcyanamide was added 100 ml of 20% methanolic ammonia and the mixture was reacted in an autoclave at 180° C. for 5 hours. The reaction mixture was concentrated to dryness, the residue was dissolved in 10 ml of methanol and the crude crystals precipitated on cooling were recrystallized from 80 ml of hot water. The above procedure provided light-brown needles of N²-(3-pyridyl)-2,6-diaminonebularine, m.p. 261°–262° C.

| Elemental analysis (C₁₅H₁₇N₇O₄) | | | |
|---|---|---|---|
| | C (%) | H (%) | N (%) |
| Calcd. | 50.14 | 4.77 | 27.28 |
| Found | 49.57 | 4.81 | 27.20 |

EXAMPLE 2

The reaction and treatment procedure of Example 1 was repeated using 3.5 g of 5-amino-4-cyano-1-(2,3,5-tri-O-propionyl-D-ribofuranosyl)imidazole, 2 g of 5-methyl-3-pyridylcyanamide and 70 ml of 20% methanolic ammonia to give N²-(5-methyl-3-pyridyl)-2,6-diaminonebularine, m.p. 287°–288° C.

| Elemental analysis (C₁₆H₁₉N₇O₄·½H₂O) | | | |
|---|---|---|---|
| | C (%) | H (%) | N (%) |
| Calcd. | 50.86 | 5.20 | 25.95 |
| Found | 50.44 | 5.09 | 25.69 |

EXAMPLE 3

A mixture of 5 g of 5-amino-1-β-D-ribofuranosyl-4-cyanoimidazole, 14 g of 2-pyridylguanidine sulfate and 50 ml of methyl-cellosolve were stirred at 130° C. for 10 hours. The reaction mixture was concentrated to dryness and the residue was recrystallized from hot water to give 3.1 g of N²-(2-pyridyl)-2,6-diaminonebularine as crystals melting at 264°–265° C.

| Elemental analysis (C₁₅H₁₇N₇O₄) | | | |
|---|---|---|---|
| | C (%) | H (%) | N (%) |
| Calcd. | 50.14 | 4.77 | 27.28 |
| Found | 49.46 | 4.78 | 27.07 |

EXAMPLES 4 TO 11

Following the reaction and purification procedures of Examples 1 to 3, the compounds (I) listed in Table 2 were produced.

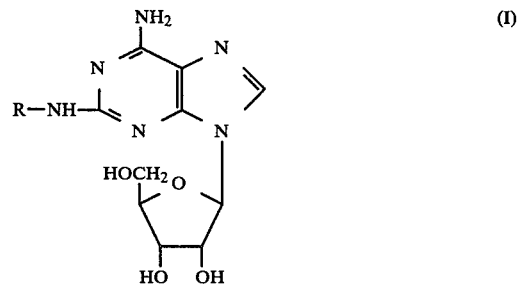

(I)

TABLE 2

| Ex. No. | R | Molecular Formula | Elemental Analysis* C(%) | H(%) | N(%) | M.P. (°C.) |
|---|---|---|---|---|---|---|
| 4 | CH₃O-pyridyl | C₁₆H₁₉N₇O₅·½H₂O | 48.79 48.71 | 4.99 4.81 | 24.89 24.99 | 143–144 |

TABLE 2-continued

| Ex. No. | R | Molecular Formula | Elemental Analysis* C(%) | H(%) | N(%) | M.P. (°C.) |
|---|---|---|---|---|---|---|
| 5 | C$_2$H$_5$O—(pyridyl)— | C$_{17}$H$_{21}$N$_7$O$_5$ | 50.62 / 50.29 | 5.25 / 5.23 | 24.31 / 24.30 | 226–227 |
| 6 | PhNH—(pyridyl)— | C$_{21}$H$_{22}$N$_8$O$_4$·½H$_2$O | 54.89 / 54.38 | 5.04 / 5.00 | 24.39 / 23.92 | 241–242 |
| 7 | (3-CH$_3$-pyridyl)— | C$_{16}$H$_{19}$N$_7$O$_4$ | 51.47 / 50.29 | 5.13 / 5.04 | 26.26 / 26.02 | 254–255 |
| 8 | (4-CH$_3$-pyridyl)— | C$_{16}$H$_{19}$N$_7$O$_4$ | 51.47 / 51.08 | 5.13 / 5.17 | 26.26 / 25.96 | 278–280 |
| 9 | (5-CH$_3$-pyridyl)— | C$_{16}$H$_{19}$N$_7$O$_4$ | 51.47 / 50.69 | 5.13 / 5.16 | 26.26 / 25.92 | 230–231 |
| 10 | (6-CH$_3$-pyridyl)— | C$_{16}$H$_{19}$N$_7$O$_4$ | 51.47 / 51.06 | 5.13 / 5.06 | 26.26 / 26.08 | 255–256 |
| 11 | (4,6-diCH$_3$-pyridyl)— | C$_{17}$H$_{21}$N$_7$O$_4$ | 52.71 / 52.20 | 5.46 / 5.69 | 25.31 / 24.62 | 268–269 |

*Calculated values in each upper row; found values in each lower row.

EXAMPLE 12

In 200 ml of 50% ethanol was suspended 8.2 g of N$^2$-(2-pyridyl)-2,6-diaminonebularine, followed by addition of 55 ml of 1 N-HCl at an elevated temperature of 60° C. to dissolve the starting compound thoroughly. This reaction mixture was concentrated to 150 ml and cooled, whereupon crystals separated out. Recrystallization from 1 l of 80% ethanol yielded N$^2$-(2-pyridyl)-2,6-diaminonebularine hydrochloride as crystals melting at 205°–208° C. (decomp.).

| Elemental analysis (C$_{15}$H$_{17}$N$_4$O$_4$·HCl·1½H$_2$O) | | | |
|---|---|---|---|
| | C (%) | H (%) | N (%) |
| Calcd. | 42.61 | 4.78 | 23.19 |
| Found | 42.14 | 4.74 | 23.36 |

EXAMPLE 13

To a solution of 0.28 g of sodium in 4 ml of methanol was added 2 g of 3-pyridyl guanidinium nitrate and the solvent was removed in vacuo. The residue was dissolved in 20 ml of 2-methoxy-ethanol, 2 g of 5-amino-1-β-D-ribofuranosyl-4-cyanoimidazole was added, and the solution was refluxed for 8 hours. The solution was evaporated to dryness in vacuo and the residue was applied on a column of 100 g of silica gel. The column was eluted with chloroform-methanol (10:1, v/v) and then with chloroform-methanol (4:1, v/v). The fractions containing the objective compound were pooled and evaporated to dryness in vacuo. The residue was recrystallized from water to give 40 mg of N$^2$-(3-pyridyl)-2,6-diaminonebularine as coloress needles, m.p. 260°–261° C.

EXAMPLE 14

When the compound (I) of this invention is used as a drug for the treatment of ischemic heart diseases such as coronary insufficiency, angina pectoris and myocardial infarction, it can be administered in the following formulations, for instance.

| 1. Tablets | |
|---|---|
| (1) N²-(3-pyridyl)-2,6-diaminonebularine | 1 mg |
| (2) Lactose | 35 mg |
| (3) Corn starch | 150 mg |
| (4) Microcrystalline cellulose | 30 mg |
| (5) Magnesium stearate | 5 mg |
| | 221 mg per tablet |

The entire amounts of (1), (2) and (3), two-thirds of the indicated amount of (4) and one-half of the indicated amount of (5) are admixed and granulated. Then, the remaining portions of (4) and (5) are added and the mixture is compression-molded into a tablet.

| 2. Capsules | |
|---|---|
| (1) N²-(5-methyl-3-pyridyl)-2,6-diaminonebularine | 1 mg |
| (2) Lactose | 100 mg |
| (3) Microcrystalline cellulose | 70 mg |
| (4) Magnesium stearate | 10 mg |
| | 181 mg per capsul |

The whole amounts of (1), (2) and (3) and one-half of the indicated amount of (4) are admixed and granulated. Then, the remaining portion of (4) is added and the mixture is filled into a gelatin capsul.

| 3. Injections | |
|---|---|
| (1) N²-(2-pyridyl)-2,6-diaminonebularine hydrochloride | 0.1 mg |
| (2) Inosit | 100 mg |
| (3) Benzyl alcohol | 20 mg |

(1), (2) and (3) are dissolved in a sufficient amount of distilled water to make 2 ml. The solution is filled into an amber-colored ampul, followed by purging with N² gas. The entire process is aseptically performed.

EXPERIMENTAL EXAMPLE

Dogs weighing 7 to 12 kg were anesthetized with pentobarbital sodium (30 mg/kg, i.v.) and, under supportive respiration, a left thoractomy was performed at the 5th intercostal space to expose the heart. An extracorporeal blood circuit is established between the femoral artery and the left coronary arterial circumflex via a polyethylene tube. The coronary blood flow was measured with an electromagnetic flow-meter (MF-2, Nippo Koden K.K.) disposed along the extracorporeal circuitry.

The test compound, as a 1 μg/ml solution in physiological saline, was administered directly into the coronary artery through the polyethylene tube at the dose of 0.3 μg/dog, and then in coronary arterial flow were measured at 30 seconds, 1 min., 2 min., 3 min. and 5 min. following the administration. The results are shown in Table 3.

The percent increase in coronary arterial flow were calculated by means of the following equation.

$$\frac{\text{Coronary blood flow at each time of measurement after administration} - \text{Coronary blood flow before administration}}{\text{Coronary blood flow before administration}} \times 100 = \% \text{ increase in Coronary blood flow}$$

TABLE 3

| Compound | Percent increase in coronary blood flow After doing | | | | |
|---|---|---|---|---|---|
| | 30 sec | 1 min | 2 min | 3 min | 5 min |
| N²-(3-pyridyl)-2,6-diamino-nebularine | 353.0 | 280.7 | 120.3 | 45.4 | 3.9 |
| N²-(5-methyl-3-pyridyl)-2,6-diamino-nebularine | 258.5 | 160.6 | 121.1 | 84.6 | 39.6 |
| N²-(6-methoxy-3-pyridyl)-2,6-diamino-nebularine | 172.1 | 77.6 | 47.7 | 24.2 | 11.2 |
| N²-(6-ethoxy-3-pyridyl)-2,6-diamino-nebularine | 188.3 | 51.5 | 30.9 | 21.6 | 14.5 |

What is claimed is:
1. A compound of the formula:

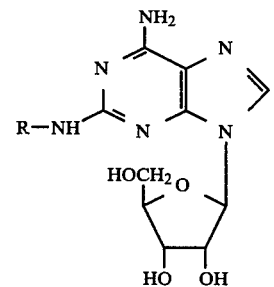

wherein R is 2-pyridyl or 3-pyridyl which may be substituted with lower alkyl, lower alkoxyl, amino, (mono- or di-$C_{1-2}$ alkyl)amino and/or anillino, or an acid addition salt thereof.

2. A compound according to claim 1, wherein R is unsubstituted 2-pyridyl or 3-pyridyl.

3. A compound according to claim 1, wherein R is 3-pyridyl which is mono-substituted with one substituent from the group of $C_{1-4}$ alkyl, $C_{1-4}$ alkoxyl, amino (mono- or di-$C_{1-2}$ alkyl)amino and anilino on its 5- or 6-position, or is disubstituted with two of said substituents on its 5- and 6-positions.

4. A compound according to claim 3, wherein the substituent is $C_{1-4}$ alkyl.

5. A compound according to claim 3, wherein the substituent is $C_{1-4}$ alkoxyl.

6. A compound according to claim 1, said compound being N²-(3-pyridyl)-2,6-diaminonebularine.

7. A compound according to claim 1, said compound being N²-(5-methyl-3-pyridyl)-2,6-diaminonebularine.

8. A compound according to claim 1, said compound being N²-(6-methoxy-3-pyridyl)-2,6-diaminonebularine.

9. A pharmaceutical composition which contains an effective amount for the treatment of ischemic heart diseases in mammals of a compound of the formula:

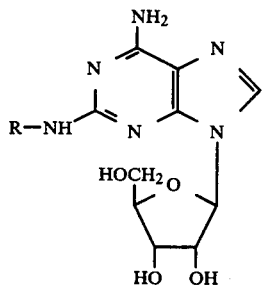

wherein R is 2-pyridyl or 3-pyridyl, which may be substituted with lower alkyl lower alkoxyl, amino, (mono- or di-$C_{1-2}$ alkyl)amino and/or anillino, or an acid addition salt thereof, and a pharmaceutically acceptable carrier, vehicle or diluent therefor.

10. A method for the treatment of ischemic heart diseases in mammal, which comprises administering to the mammal an effective amount of a compound of the formula:

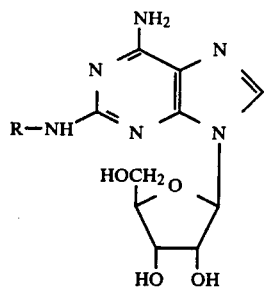

wherein R is 2-pyridyl or 3-pyridyl, which may be substituted with lower alkyl, lower alkoxyl, amino, (mono- or di-$C_{1-2}$ alkyl)amino or/and anillino, or an acid addition salt thereof.

* * * * *